United States Patent
Dubois et al.

(10) Patent No.: US 6,606,909 B2
(45) Date of Patent: Aug. 19, 2003

(54) METHOD AND APPARATUS TO CONDUCT ULTRASONIC FLAW DETECTION FOR MULTI-LAYERED STRUCTURE

(75) Inventors: Marc Dubois, Clifton Park, NY (US); Peter William Lorraine, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/931,122

(22) Filed: Aug. 16, 2001

(65) Prior Publication Data

US 2003/0033878 A1 Feb. 20, 2003

(51) Int. Cl.$^7$ .............................................. G01N 29/02
(52) U.S. Cl. ............................ 73/600; 73/579; 73/598; 73/602; 73/643
(58) Field of Search ......................... 73/600, 579, 597, 73/602, 604, 618, 624, 643, 598, 599

(56) References Cited

U.S. PATENT DOCUMENTS

| | | | | |
|---|---|---|---|---|
| 4,301,684 A | * | 11/1981 | Thompson et al. ........... | 73/602 |
| 4,976,150 A | * | 12/1990 | Deka .......................... | 73/644 |
| 5,167,157 A | * | 12/1992 | Wertz et al. .................. | 73/627 |
| 5,476,010 A | | 12/1995 | Fleming et al. ............... | 73/620 |
| 5,495,763 A | | 3/1996 | Rhodes et al. ................ | 73/579 |
| 5,760,904 A | * | 6/1998 | Lorraine et al. ............. | 356/513 |
| 5,801,312 A | * | 9/1998 | Lorraine et al. ............. | 600/443 |
| 5,824,908 A | * | 10/1998 | Schindel et al. .............. | 73/598 |
| 5,837,896 A | | 11/1998 | Rhodes et al. ................ | 73/579 |
| 5,929,337 A | * | 7/1999 | Collins et al. ............... | 209/590 |
| 6,057,927 A | * | 5/2000 | Levesque et al. ............ | 356/432 |
| 6,092,419 A | * | 7/2000 | Dixon et al. .............. | 250/231.1 |
| 6,109,108 A | * | 8/2000 | Ohtani et al. ................. | 76/599 |
| 6,128,081 A | * | 10/2000 | White et al. ................ | 356/432 |
| 6,182,512 B1 | * | 2/2001 | Lorraine ..................... | 73/602 |
| 6,234,025 B1 | | 5/2001 | Gieske et al. ................. | 73/642 |
| 6,367,328 B1 | * | 4/2002 | Gorman et al. ........... | 73/209 R |

* cited by examiner

Primary Examiner—Helen Kwok
Assistant Examiner—Jacques Saint-Surin
(74) Attorney, Agent, or Firm—Hughes & Luce LLP

(57) ABSTRACT

An invention to measure of objects of non-homogeneous ultrasonic impedance in the testing path is provided to detect the present of flaws in any part of the object. The invention utilized a reference signal to compare against the actual signal derived from ultrasonic testing of the object. Reference signals are determined based upon the known or calculated properties of the object's layers or previously obtained signals measured from the object.

40 Claims, 4 Drawing Sheets

ABSTRACT / PATENT TEXT

METHOD AND APPARATUS TO CONDUCT ULTRASONIC FLAW DETECTION FOR MULTI-LAYERED STRUCTURE

BACKGROUND OF THE INVENTION

1. Technical Field

This invention relates generally to material testing and more particularly to nondestructive detection of flaws in objects. A flaw may be a crack in an object, a void in an object and/or a deviation from dimensional specifications of the object, and any other parameter that causes a change in mechanical resonance.

2. Description of the Related Art

FIG. 1 shows an example of an ultrasonic signal (A-Scan) used to detect a defect within a single layered object. The time window 101 is typically determined by the thickness of the object, so that backwall echo 105 is excluded from the ultrasonic scan. FIG. 1 shows an ultrasonic signal in A-scan mode and presents a typical defect echo 110 within the time window 101.

In the case of objects with layers comprising of different ultrasonic impedances for the ultrasonic signal path, this simple detection scheme cannot be used, because at no time is a window present where the signal is zero. This makes it extremely difficult, time consuming and cost prohibitive to detect a defect echo with confidence.

FIG. 2 shows a typical experimental ultrasonic echo signal (A-Scan) obtained from a 3-layered object, where each layer has a different impedance and wherein the object is without defect. This signal, when compared to the signal in FIG. 1, is considered a complex signal. If a defect was present, the signal would be hardly distinguishable from the signal in FIG. 2, which is without defect.

Traditionally, this type of multi-layered object is ultrasonically tested in transmission configuration. In the transmission configuration, the ultrasound generator is placed on one side of the part and the ultrasound detector is placed on the other side. Defects are detected by a significant decrease in the transmitted ultrasonic signal. However, in many cases, the inspection can only be performed from a single side and the transmission technique cannot be used.

FIG. 2A shows a typical experimental ultrasonic signal (B-Scan) obtained from a 3-layered object wherein one lone defect is present.

BRIEF SUMMARY OF THE INVENTION

The invention presents a flaw detection apparatus for detecting flaws within a multi-layered object comprising an object wherein the ultrasonic impedance varies across the ultrasonic signal path of the object and such variance is not due to a defect, a means for collecting an actual signal from an ultrasonic test conducted on the object, a reference signal for the object, a means for comparing the actual signal to the reference signal, and a display means for displaying the comparison signal.

Additionally, the invention presents a method to detect flaws within a object comprising the steps of producing an actual ultrasonic test signal for the object, comparing the actual signal to a reference signal for the object, and displaying the compared results.

Additionally, the invention presents an apparatus for performing ultrasonic testing of an object, the apparatus comprising a means for receiving an actual ultrasonic signal from the object, a means for comparing the actual signal to a reference signal for the object and a means for displaying the comparison result.

The foregoing has outlined some of the more pertinent objects and features of the present invention. These objects should be construed to be merely illustrative of some of the more prominent features and applications of the invention. Applying the disclosed invention in a different manner can attain many other beneficial results or modifying the invention as will be described. Accordingly, other objects and a fuller understanding of the invention may be had by referring to the following Detailed Description of the Preferred Embodiment.

BRIEF DESCRIPTION OF THE DRAWINGS

For a more complete understanding of the present invention and the advantages thereof, reference should be made to the following Detailed Description taken in connection with the accompanying drawings in which.

DETAILED DESCRIPTION OF THE PREFERRED EMBODIMENT

The invention comprises of a system and process for interpreting complex ultrasonic echo signals from objects whose impedance varies across the ultrasonic transmission/echo path.

In the present invention a reference signal is used to compare against an ultrasonic test's actual signal to determine if a defect exists. The reference signal can be created by using a synthetic computed reference signal, a signal from a database containing synthetic signals or experimental signals from reference parts, or a signal averaged from the tested part. If a synthetic computer reference signal or a database reference signal is used, the signal must be corrected for the ultrasonic phase and amplitude response versus frequency of the experimental system currently used (like response of the detector and electronics). The advantage of using an averaged signal from the currently inspected part is that such corrections are not necessary.

Figure 1:
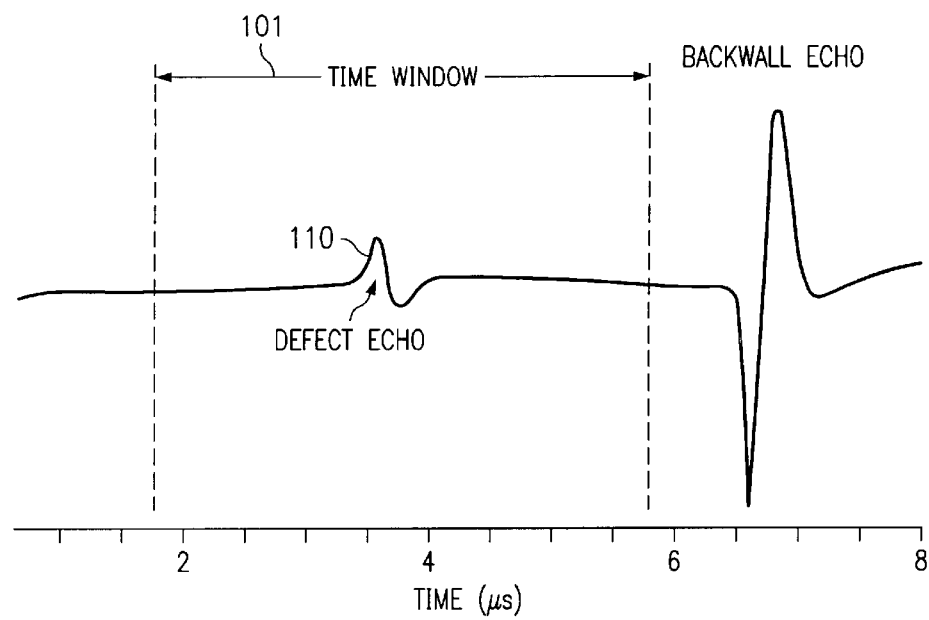
FIG. 1 shows an example of an ultrasonic signal (A-scan) used to detect a defect within a single layered object.
Figure 2:
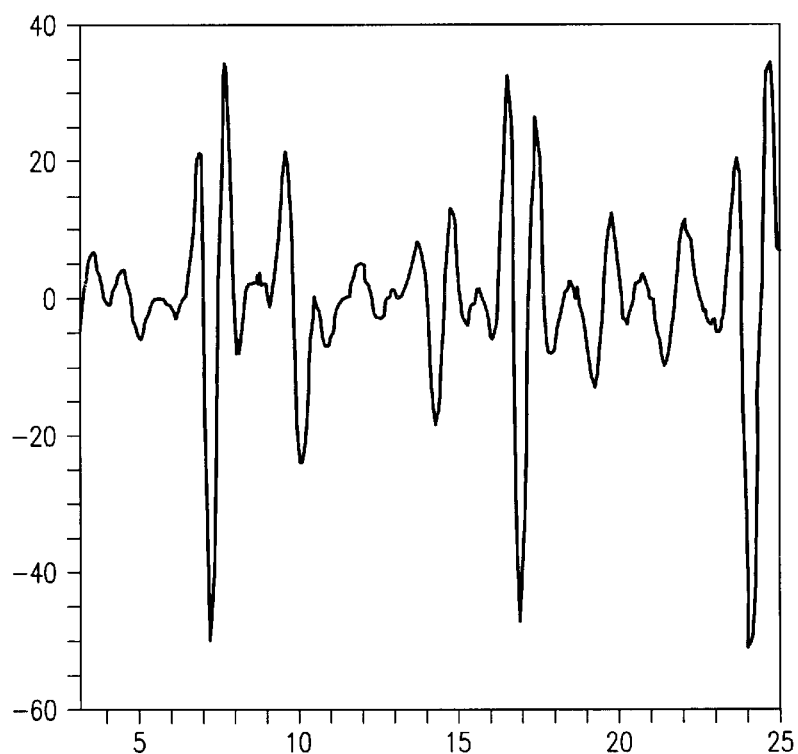
FIG. 2 shows a typical experimental ultrasonic signal (A-scan) obtained from a 3-layered object wherein the object is without defect.
Figure 2A:
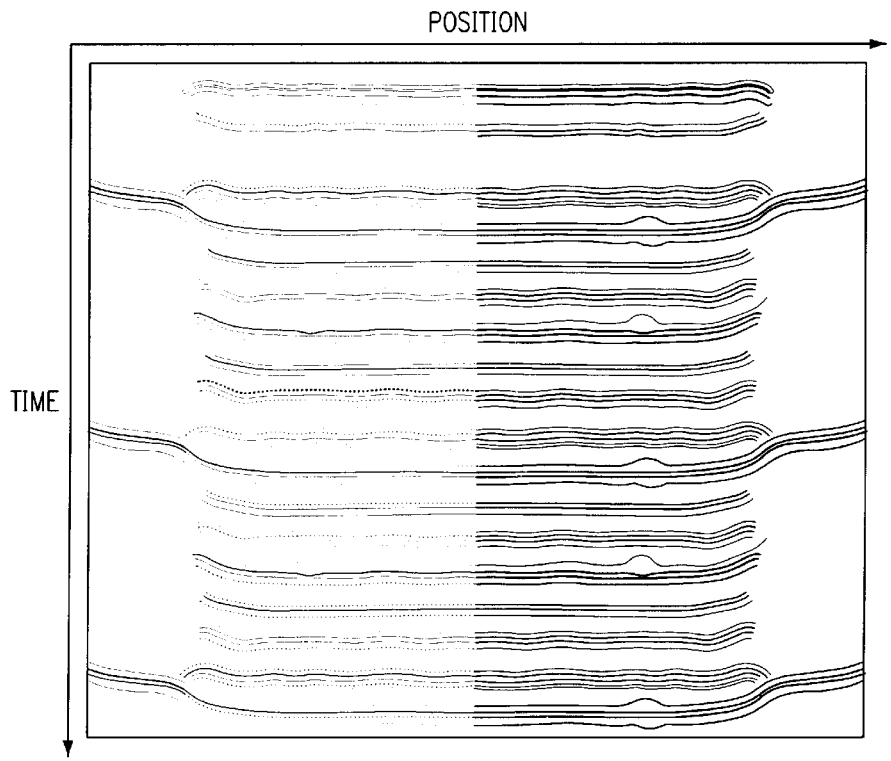
FIG. 2A shows a typical experimental ultrasonic B-scan obtained from a 3-layered object wherein one defect is present.
Figure 3A:
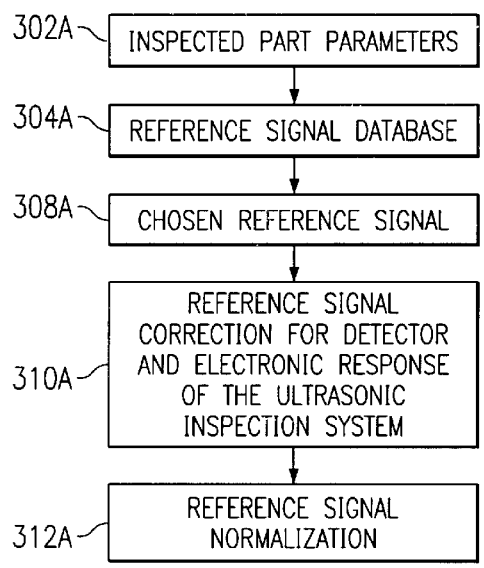
FIG. 3A shows a block diagram of the methodology utilized to obtain a reference signal generated by computer.

FIG. 3A shows a block diagram of the methodology utilized to obtain a reference signal from a database. In step 302A, the object's parameters are determined. Once the parameters are know, then, in step 304A, a reference signal database is accessed to chose the signal that best fits the object's parameters. Once a reference signal with the correct parameters are chosen in step 308A, the reference signal is corrected for detector and electronic response of the ultrasonic inspection system in step 310A. Thereupon, the reference signal is normalized in step 312A.

If the type of the inspected object is not known, a bank of reference signals (calculated and/or experimental) can be used, and the signal from the bank, which closely matches the actual result or signal, should be used as a reference signal. The chosen reference signal then provides information against which the actual signal is compared for the type of object currently inspected.

Figure 3B:
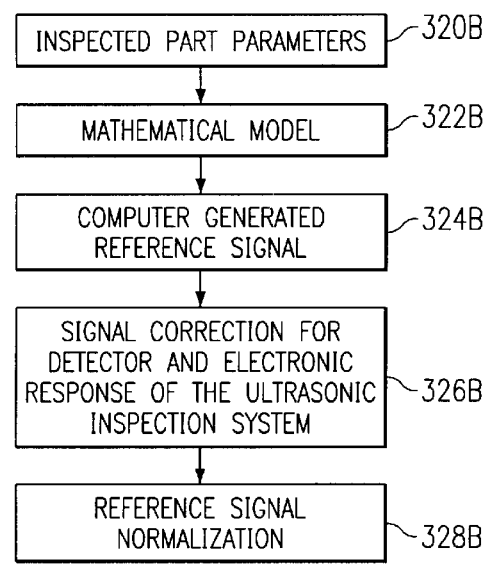
FIG. 3B shows a block diagram of the methodology utilized to obtain a reference signal from a database.

FIG. 3B shows a block diagram of the methodology utilized to obtain a reference signal generated by a computer. In this methodology, the object's parameters are determined for testing in step 320B. Once known, a mathematical model is generated to describe the aspects of the object to be tested in step 322B. The mathematical model, then is utilized to generate a reference signal from the computer database based on the objects parameters as described in the mathematical model. Once the reference signal is generated, the signal is corrected for detector and electronic response of the ultrasonic inspection system in step 324B. Thereupon, the reference signal is normalized in step 328B.

If the precise type of object inspected is not known, or if no reference signal bank is available, an experimental signal from the inspected part can be used as the reference.

Figure 3C:
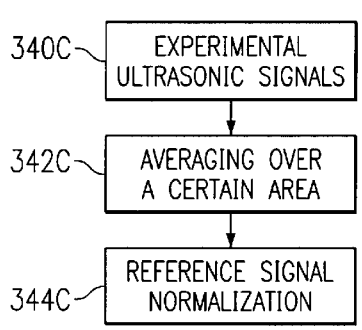
FIG. 3C shows a block diagram of the methodology utilized to obtain a reference signal from the signals averaged from an area of the currently inspected part.

FIG. 3C shows a block diagram of the methodology utilized to obtain a reference signal from the signals averaged from an area of the currently inspected part. In step 340C, a group of experimental signals are taken for the object in an area known to be defect free, if possible. Once taken, the experimental signals are averaged over a certain area in step 342C to reduce fluctuations in the material composition for received in any one experimental test. Thereupon, the experimental reference signal is normalized in step 344C.

Before the comparison, the measured signal needs to be normalized using the same algorithm as the one used for the reference signal. An easy way is to normalize the signal according to the maximum of the signal in the time-window. Other normalization schemes can be used as well.

Figure 3D:
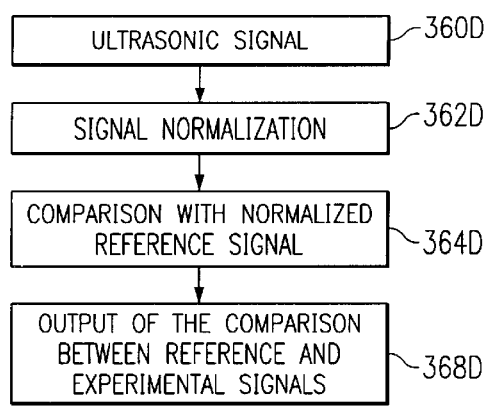
FIG. 3D shows a block diagram of the methodology utilized to compare the experimental signal with the reference signal.

FIG. 3D shows a block diagram of the methodology utilized to compare the experimental signal with the reference signal. In step 360D, an ultrasonic signal is taken for the inspected object. Once taken, the signal is normalized in step 362D and then compared with the reference signal in step 364D. The output of the comparison between the reference signal and the ultrasonic test's actual signal are then analyzed to determine if a defect exists in step 368D.

Once the comparison is complete, the resultant signal is displayed on a display device, such as a computer screen, a printout, or monitor so that the results may be viewed and analyzed. It is important to note that the actual signal need not be stored and that the actual signal can be compared against the reference signal in real time as the actual signal is being produced.

As in the inspection on single layer of non-homogeneous or uniform impedance across the ultrasonic signal path, a time-window for the signal must be determined starting at time $t_1$ and finishing at time $t_2$. This time-window is set similarly to conventional inspection, such that the time-window is set between the beginning of the signal and the first ultrasonic echo coming from the back wall of the last layer of the object if it is a multi-layered object, the signal optionally including the back wall echo. The time-window can be set differently if some depth of the object needs to be inspected more or less specifically. The signal in this time-window is compared to the signal of the reference signal within the same time-window. There are various ways to compare the measured signal ($z_{meas}(t)$) to the reference signal ($z_{ref}(t)$). The measured signal and the reference signal can be subtracted against each other and summed over time using the below algorithm:

$$\text{Result} = \sum_{t=t_1}^{t=t_2} z_{meas}(t) - z_{ref}(t)$$

they can be summed together using the below algorithm:

$$\text{Result} = \sum_{t=t_1}^{t=t_2} z_{meas}(t) + z_{ref}(t)$$

or multiplied data point by data point and summed using the below algorithm:

$$\text{Result} = \sum_{t=t_1}^{t=t_2} z_{meas}(t) * z_{ref}(t)$$

or subtracted data point by data point and squared and summed using the below algorithm:

$$\text{Result} = \sum_{t=t_1}^{t=t_2} (z_{meas}(t) - z_{ref}(t))^2$$

or the comparison can be accomplished using any other known comparison or statistical method to flush out the defects. The result of the comparison is used in a traditional amplitude measurement for inspection of single homogeneous layer material.

Figure 4A:
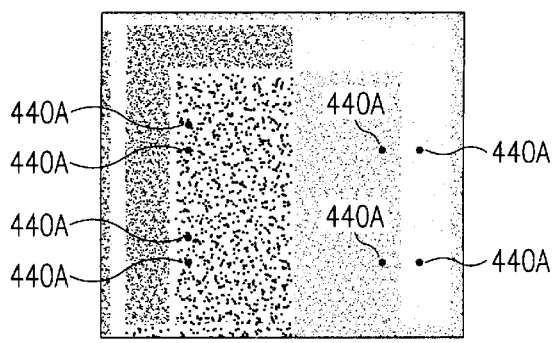
FIG. 4A shows an image produced by the traditional amplitude measurement in a c-scan format.
Figure 4B:
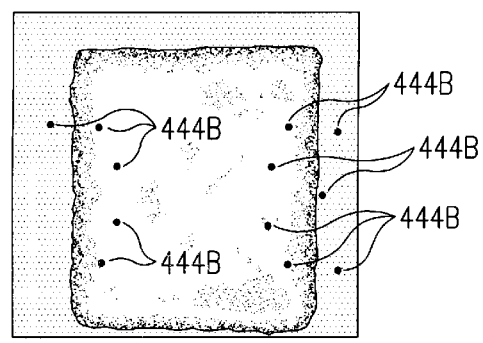
FIG. 4B shows a c-scan obtained using comparison with an experimental reference signal.

FIG. 4A shows an image produced by the traditional amplitude measurement in a c-scan format. FIG. 4B shows a c-scan obtained using comparison with a reference signal. The measured signals were multiplied point by point by the reference signal in the chosen time-window and summed to produce image 450.

Figure 4C:
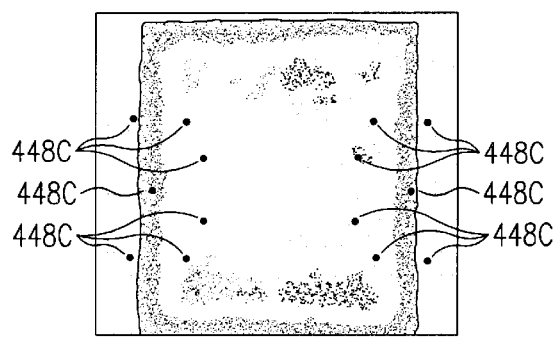
FIG. 4C shows a c-scan obtained using comparison with a computer-generated reference signal.

In FIG. 4B, the reference signal was derived by using an experimental measured signals. Similar results are obtained using a computer-generated reference signal. FIG. 4C shows an image produced using a computer-generated reference signal for the same material.

The sample used in FIGS. 4A & 4B & 4C is a 3-layer graphite-epoxy/syncore/graphite-epoxy object with a 2-layer graphite-epoxy/graphite-epoxy object near the upper left, and upper right edges, with 2 different peel plies on the left and right sides, and with 14 known defects, 7 defects on each side of center, near the 2-layer/3-layer delimitation.

FIGS. 4A & 4B shows the advantage of the invention. FIG. 4A shows detection of 8 of the 14 defects 440A. However, it must be noted that this method, even some of these defects are not clearly detected. The remaining defects are not detected.

FIG. 4B, analyzing the same object, shows the detection of the 14 defects. Furthermore, FIG. 4B shows some characteristics of certain aspects of the object like the number of peel plies in the lower part of the image and the orientation of the fibers.

In FIG. 4C as in FIG. 4B, all 14 defects are detected. However, FIG. 4C shows more defect contrast than FIG. 4B but less sensitivity to small details like ply number of fiber orientation. This difference is explained by the difficulty in computer-generating a signal that matches all the subtleties of the experimental signals such as electronic response, surface variations, laser variations, etc. However, while being less sensitive to small details, using a computer-generated signal for a reference produces a better contrast for defect detection.

Figure 5A:
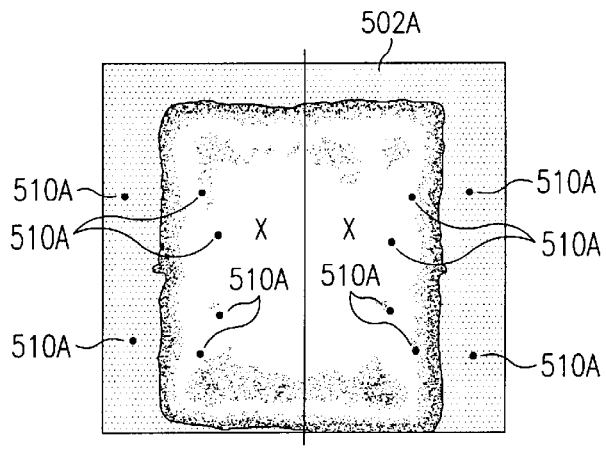
FIG. 5A shows a c-scan obtained by using comparison of different experimental reference signals from the 3-layer zones for each side of the c-scan.
Figure 5B:
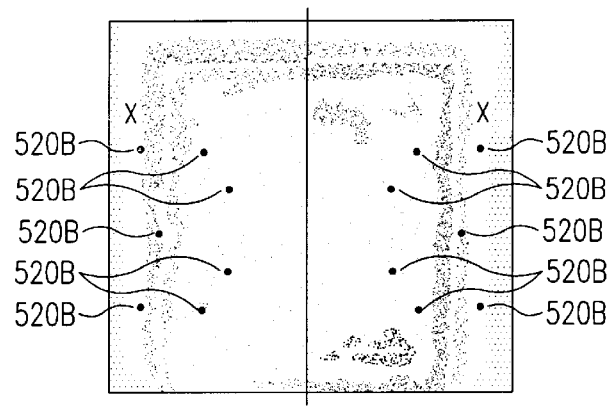
FIG. 5B shows a C-scan obtained by using comparison of different experimental reference signals coming from the 2-layer zones for each side of the c-scan.

FIG. 4B used a single reference signal to detect defects over the whole inspected area. Knowledge of the layer geometry for the entire object being tested is more efficient because a different reference signal may be used for each part of the object that has a different layered or impedance arrangement. In the case of FIG. 4B, four different reference signals could be used: two references signal for the left area and two for the right area: one for where there is only 2 layers and one for the area where there are 3 layers. FIGS. 5A & 5B gives an example of that process for the same part of FIGS. 4A, 4B and 4C.

FIGS. 5A & 5B shows the result for same object as in FIGS. 4A, 4B, and 4C using multiple reference signals. FIGS. 5A & 5B shows that detection can be significantly improved in each area using a reference signal from specified areas for those areas. FIGS. 5A & 5B shows the 14 defects, 510A and 520B, which are clearer and more detectable using the multiple reference signal process.

In the case of an object with continuously changing parameters like thickness or number of plies, the reference signal can be changed continuously by taking one reference signal for each column of data. The choice of the reference signal can be automated using the CAD data of the part.

FIG. 5A shows reference signals from a 3-layer area 502A and FIG. 5B shows reference signals from the 2-layer area 504B. For each image, the left part used a reference signal from the left area of the part, and the right part used a reference signal from the right area of the part. A "X" in FIGS. 5A and 5B indicates where the reference signal comes from for each image.

Figure 6:
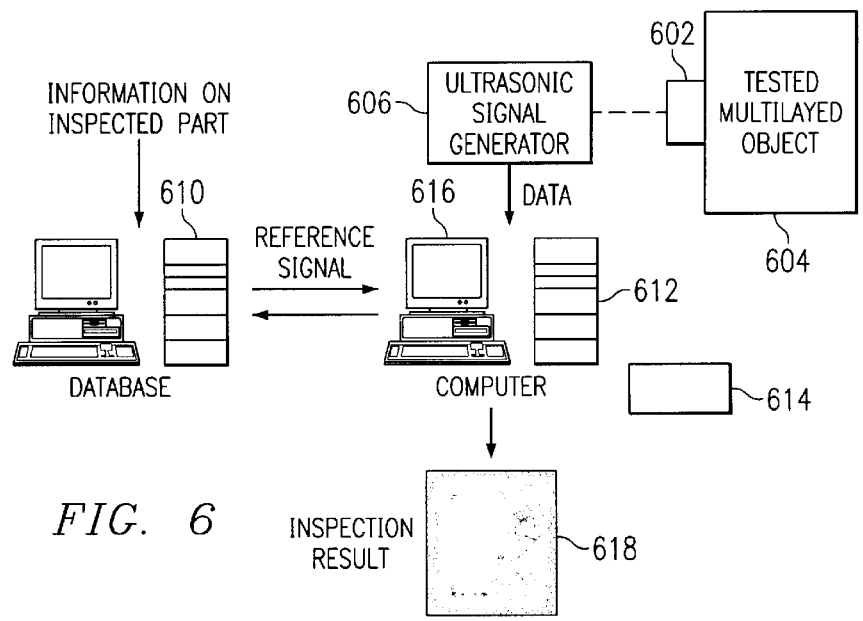
FIG. 6 shows a diagram of the present invention as utilized in a ultrasonic testing system.

FIG. 6 shows a diagram of the present invention as utilized in a ultrasonic testing system. An ultrasonic device 602 such as used in either a laser-ultrasound, a piezoelectric transducer, a electromagnetic transducer or an air-coupled transducer is used to generate ultrasound in the object 604. A signal generator, 606 produces a signal through the object and the actual return echo signal is received by the device 602. For a simple object, a time window is set on the ultrasonic signal between the beginning of the signal and the back wall echo. The signal amplitude inside the time window is measured. If a defect is present in the object, an echo appears in the time window.

The actual signal may be recorded into a database 608 for later comparison to a reference signal, which may be located in a different database 610. Or the actual signal may be compared as it is read by transducer 602 with database 610, by a comparison device such as computer 612. Computer 612 may use algorithms, such as those described above, to compare the reference signal to the actual signal. Once the comparison is complete, the comparison result 618 is displayed by computer 612, either on a printout 614, a computer screen 616, or other display means as an operator may choose and is commonly available to computer systems such as described here.

Having thus described our invention, what we claim as new and desire to secure by Letters Patent is set forth in the following claims.

What is claimed is:

1. A flaw detection system comprising of:
   an object having an impedance path across an ultrasonic signal path;
   a means for collecting an actual ultrasonic signal from an ultrasonic test conducted on the object;
   a reference signal for the object;
   a means for comparing the actual signal to the reference signal, wherein the means for comparing the actual signal to the reference signal further comprises a means for determining the difference between the actual signal and the reference signal by subtracting each actual resultant point as a function of time from each corresponding reference resultant point as a function of the time and summing all differences over the time window; and
   a display means for displaying the comparison signal.

2. The system of claim 1 wherein the means to collect the signal is a laser-ultrasound system.

3. The system of claim 1 wherein the means to collect the signal is an ultrasonic system based on piezoelectric transducers.

4. The system of claim 1 wherein the means to collect the signal is an electromagnetic transducer.

5. The system of claim 1 wherein the means to collect the signal is air-coupled transducers.

6. The system of claim 1 wherein the object comprises of a multi-layered object.

7. The system of claim 1 wherein the object generates a complex echo from an ultrasonic, wherein the complex echo is not due to a defect.

8. The system of claim 1 wherein the reference signal comprises of a compiled signal based on known qualities of the object.

9. The system of claim 1 wherein the reference signal comprises of an ultrasonic signal from a known part of the object.

10. The system of claim 1 wherein the reference signal comprises of a bank of ultrasonic signals that closely match the actual signal.

11. The system of claim 1 wherein the reference signal is automatically chosen among the signals in a bank based on features of the actual signal.

12. The system of claim 1 wherein the reference signal is a calculated signal based on known qualities of the object.

13. The system of claim 1 wherein the reference signal is calculated based on features of the actual signal measured on the object.

14. The system of claim 1 wherein the reference signal comprises of an experimental signal from the object.

15. The system of claim 1 wherein different reference signals are used for different areas of the object such that a first reference signal is used for a first areas of the object, a second signal is used for a second areas of the object, each signal presenting characteristics associated with its corresponding area of the object.

16. The system of claim 1 wherein the display means displays the comparison result in an A-scan mode.

17. The system of claim 1 wherein the display means displays the comparison result in a B-scan mode.

18. The system of claim 1 wherein the display means displays the comparison result in a C-scan mode.

19. The system of claim 1 wherein the impedance varies across the ultrasonic signal path, wherein the variance is not due to a defect.

20. A method to detect flaws comprising the steps of:
collecting an actual signal of an ultrasonic test of an object;
comparing the actual signal to a reference signal of the object, wherein comparing the actual signal to the reference signal further comprises a means for determining the difference between the actual signal and the reference signal by subtracting each actual resultant point as a function of time from each corresponding reference resultant point as a function of the time and summing all differences over the time window; and
displaying the compared results.

21. The method of claim 20 wherein the object contains a varying impedance across an actual ultrasonic signal path.

22. The method of claim of step 20 wherein the object is a multi-layered object.

23. The method of claim 20 wherein the collecting comprises of conducting a laser-ultrasonic test.

24. The method of claim 20 wherein the collecting comprises of using piezoelectric transducers for the ultrasonic signal.

25. The method of claim 20 wherein the collecting comprises of using electromagnetic transducers for the ultrasonic signal.

26. The method of claim 20 wherein the collecting comprises of using air-coupled transducers for the ultrasonic signal.

27. The method of claim 20 wherein the actual signal in the collecting step comprises of a complex actual signal.

28. The method of claim 20 further comprising the step of producing a reference signal, wherein the reference signal comprises of a bank of signals that closely match the actual signal.

29. The method of claim 20 further comprising the step of producing a reference signal, wherein the reference signal is automatically chosen among signals in a signal bank based on features of the actual signal.

30. The method of claim 20 further comprising the step of producing a reference signal wherein the reference signal is a calculated signal based on known qualities of the object.

31. The method of claim 20 further comprising the step of producing a reference signal wherein the reference signal is calculated based on features of the actual signal measured on the object.

32. The method of claim 20 further comprising the step of producing a reference signal wherein different reference signals are used for different areas of the object.

33. An apparatus for performing ultrasonic testing of an object, the apparatus comprising:
a means for receiving an actual ultrasonic signal from the object;
a means for comparing the actual signal to a reference signal for the object, wherein the means for comparing the actual signal to the reference signal further comprises a means for determining the difference between the actual signal and the reference signal by subtracting each actual resultant point as a function of time from each corresponding reference resultant point as a function of the time and summing all differences over the time window; and
a means for displaying the comparison result.

34. The apparatus in claim 33 wherein the object has a varying impedance across the actual signal path, wherein the variance is not due to a defect in the object.

35. A flaw detection system comprising of:
an object having an impedance path across an ultrasonic signal path;
a means for collecting an actual ultrasonic signal from an ultrasonic test conducted on the object;
a reference signal for the object;
a means for comparing the actual signal to the reference signal, wherein the means for comparing the actual signal to the reference signal further comprises of a means for determining the sum of the actual signal and the reference signal by adding each actual resultant point as a function of time to corresponding each reference signal point as a function of the time and summing all sums over the time window; and
a display means for displaying the comparison signal.

36. A flaw detection system comprising of:
an object having an impedance path across an ultrasonic signal path;
a means for collecting an actual ultrasonic signal from an ultrasonic test conducted on the object;
a reference signal for the object;
a means for comparing the actual signal to the reference signal, wherein the means for comparing the actual signal to the reference signal further comprises of a means for determining the product of the actual signal and the reference signal by multiplying each actual resultant point as a function of time to each corresponding reference signal point as a function of time and summing all products over the time window; and
a display means for displaying the comparison signal.

37. A flaw detection system comprising of:
an object having an impedance path across an ultrasonic signal path;
a means for collecting an actual ultrasonic signal from an ultrasonic test conducted on the object;
a reference signal for the object;
a means for comparing the actual signal to the reference signal, wherein the means for comparing the actual signal to the reference signal further comprises of a means for determining the difference between the actual signal and the reference signal by subtracting each actual resultant point as a function of time from each corresponding reference resultant point as a function of the time, squaring each difference and summing all squares over the time window; and
a display means for displaying the comparison signal.

38. A method to detect flaws comprising the steps of:
collecting an actual signal of an ultrasonic test of an object;
comparing the actual signal to a reference signal of the object, wherein comparing the actual signal to the reference signal further comprises:
adding each actual resultant point as a function of time to corresponding each reference result point as a function of the time; and
summing all differences over the time window; and displaying the compared results.

39. A method to detect flaws comprising the steps of:

collecting an actual signal of an ultrasonic test of an object;

comparing the actual signal to a reference signal of the object, wherein comparing the actual signal to the reference signal further comprises:
- multiplying each actual resultant point as a function of time to each corresponding reference signal point as a function of time; and
- summing all differences over the time window; and displaying the compared results.

40. A flaw detection system comprising of:

an object having an impedance path across an ultrasonic signal path;

a means for collecting an actual ultrasonic signal from an ultrasonic test conducted on the object;

a reference signal for the object;

a means for comparing the actual signal to the reference signal, wherein the means for comparing the actual signal to the reference signal is selected from the group of means consisting of:
- a means for determining the difference between the actual signal and the reference signal by subtracting each actual resultant point as a function of time from each corresponding reference resultant point as a function of the time and summing all differences over the time window;
- a means for determining the sum of the actual signal and the reference signal by adding each actual resultant point as a function of time to corresponding each reference signal point as a function of the time and summing all sums over the time window;
- a means for determining the product of the actual signal and the reference signal by multiplying each actual resultant point as a function of time to each corresponding reference signal point as a function of time and summing all products over the time window;
- a means for determining the difference between the actual signal and the reference signal by subtracting each actual resultant point as a function of time from each corresponding reference resultant point as a function of the time, squaring each difference and summing all squares over the time window; and a display means for displaying the comparison signal.

* * * * *